United States Patent
Marschner et al.

(10) Patent No.: US 10,249,065 B2
(45) Date of Patent: Apr. 2, 2019

(54) METHOD AND DEVICE FOR MAGNETIC RESONANCE IMAGING WITH IMPROVED SENSITIVITY BY NOISE REDUCTION

(71) Applicant: Max-Planck-Gesellschaft zur Foerderung der Wissenschaften e. V., Munich (DE)

(72) Inventors: Henrik Marschner, Leipzig (DE); Andre Pampel, Leipzig (DE); Harald Moeller, Leipzig (DE)

(73) Assignee: Max-Planck-Gesellschaft zur Foerderung der Wissenschaften e.V, Munich (DE)

( * ) Notice: Subject to any disclaimer, the term of this patent is extended or adjusted under 35 U.S.C. 154(b) by 0 days.

(21) Appl. No.: 15/572,009

(22) PCT Filed: May 8, 2015

(86) PCT No.: PCT/EP2015/000957
§ 371 (c)(1),
(2) Date: Nov. 6, 2017

(87) PCT Pub. No.: WO2016/180429
PCT Pub. Date: Nov. 17, 2016

(65) Prior Publication Data
US 2018/0089863 A1   Mar. 29, 2018

(51) Int. Cl.
*G06K 9/00* (2006.01)
*G06T 11/00* (2006.01)
(Continued)

(52) U.S. Cl.
CPC ............ *G06T 11/005* (2013.01); *A61B 5/055* (2013.01); *A61B 5/7203* (2013.01);
(Continued)

(58) Field of Classification Search
CPC . G06T 2207/10088; G06T 2207/20064; G06T 2207/30016; G06T 5/002;
(Continued)

(56) References Cited

U.S. PATENT DOCUMENTS

| 6,741,739 | B1 | 5/2004 | Vincent |
| 2008/0166064 | A1* | 7/2008 | Fu ............................ G06K 9/40 |
| | | | 382/276 |

(Continued)

FOREIGN PATENT DOCUMENTS

| CN | 102800057 | * 11/2012 | ......... G01R 33/5608 |
| CN | 102800057 A | 11/2012 | |

OTHER PUBLICATIONS

Zaroubi et al, ("Complex denoising of MR data via wavelet analysis: Application for functional MRI", Magnetic Resonance Imaging 18 (2000) 59-68, Elsevier Science Inc (Year: 2000).*
(Continued)

*Primary Examiner* — Amara Abdi
(74) *Attorney, Agent, or Firm* — Caesar Rivise, PC

(57) ABSTRACT

A method of image processing of magnetic resonance (MR) images for creating de-noised MR images, comprises the steps of providing image data sets including multiple complex MR images (S7), subjecting the MR images to a wavelet decomposition (S12) for creating coefficient data sets of wavelet coefficients ($S_{n,m}$) representing the MR images in a wavelet frequency domain, calculating normalized coefficient data sets of wavelet coefficients Formula (I) (S17), wherein the coefficient data sets are normalized with a quantitative amount of variation, in particular standard deviation Formula (II), of noise contributions included in the coefficient data sets ($S_{n,m}$), averaging the wavelet coefficients of each coefficient data set (S18) for providing averaged wavelet coefficients Formula (III) of the coefficient
(Continued)

data sets, calculating phase difference maps ($\Delta\phi_{n,m}$) for all coefficient data sets (S20), wherein the phase difference maps provide phase differences between the phase of each wavelet coefficient and the phase of the averaged wavelet coefficients Formula (III), calculating scaled averaged coefficient data sets of wavelet coefficients by scaling the averaged wavelet coefficients Formula (III) with scaling factors ($C_{n,m}$), which are obtained by comparing parts of the normalized wavelet coefficients of the normalized coefficient data sets Formula (I) that are in phase with the averaged wavelet coefficients Formula (III) (S22), calculating rescaled coefficient data sets of wavelet coefficients Formula (IV) (S24) by applying a transfer function Formula (V) on the coefficient data sets ($S_{n,m}$) and on the scaled averaged coefficient data sets, wherein the transfer function includes combined amplitude and phase filters, each depending on the normalized coefficient data sets Formula (I) and me phase difference maps ($\Delta\phi_{n,m}$), resp., and subjecting the rescaled coefficient data sets to a wavelet reconstruction Formula (IV) (S25) for providing the denoised MR images.

15 Claims, 10 Drawing Sheets

(51) Int. Cl.
| | |
|---|---|
| *G01R 33/56* | (2006.01) |
| *G06T 5/00* | (2006.01) |
| *G06T 5/10* | (2006.01) |
| *A61B 5/055* | (2006.01) |
| *A61B 5/00* | (2006.01) |
| *G01R 33/565* | (2006.01) |
| *G06T 3/00* | (2006.01) |

(52) U.S. Cl.
CPC ... *G01R 33/5608* (2013.01); *G01R 33/56545* (2013.01); *G06T 5/002* (2013.01); *G06T 5/10* (2013.01); *G06T 3/0068* (2013.01); *G06T 2207/10088* (2013.01); *G06T 2207/20064* (2013.01); *G06T 2207/30016* (2013.01)

(58) Field of Classification Search
CPC ....... G06T 5/10; G06T 3/0068; G06T 11/005; G01R 33/5608; G01R 33/56545; A61B 5/055; A61B 5/7203
See application file for complete search history.

(56) References Cited

U.S. PATENT DOCUMENTS

2014/0212015 A1* 7/2014 Ding .................. G06T 5/50
382/131

2016/0284064 A1* 9/2016 Morofuji ............ H04N 5/23238
2017/0000423 A1* 1/2017 Addison .............. A61B 5/0205

OTHER PUBLICATIONS

Vanathe et al (MR Image denoising and enhancing using multiresolution image decomposition technique, 2013 International Conference on Signal Processing, Image Processing and Pattern Recognition, IEEE 2013, pp. 1-5 (Year: 2013).*
Alexander et al. (2000). A wavelet-based method for improving signal-to-noise ratio and contrast in MR images. Magnetic Resonance Imaging, 18(2), 169-180.
Anand et al. (2010). Wavelet domain non-linear filtering for MRI denoising. Magnetic Resonance Imaging, 28(6), 842-861.
Bartusek et al. (2011). Wavelet-based de-noising techniques in MRI. Computer methods and programs in biomedicine, 104(3), 480-488.
Bullmore et al. (2004). Wavelets and functional magnetic resonance imaging of the human brain. Neuroimage, 23, S234-S249.
Chang et al. (2000). Spatially adaptive wavelet thresholding with context modeling for image denoising. IEEE Transactions on Image Processing, 9(9), 1522-1531.
Den Dekker et al. (2014). Data distributions in magnetic resonance images: A review. Physica Medica, 30(7), 725-741.
Fuchs et al. (2001). Physicians' views of the relative importance of thirty medical innovations. Health Affairs, 20(5), 30-42.
Henkelman et al. (1985). Measurement of signal intensities in the presence of noise in MR images. Med. Phys. 12 (2), 232-233.
Hoult, D. (1996). Sensitivity of the NMR experiment. In: D.M. Grant, R.K. Harris (eds.); Encyclopedia of Nuclear Magnetic Resonance, vol. 7, pp. 4256-4266, Wiley, Chichester.
Jaramillo et al. (2014). Improving the performance of the Prony method using a wavelet domain filter for MRI denoising. Computational and mathematical methods in medicine, 1-11.
Kovesi, P. (1999). Image features from phase congruency. Videre: Journal of computer vision research, 1(3), 1-26.
Mueller et al. (2013). Matrix-algebra-based calculations of the time evolution of the binary spin-bath model for magnetization transfer. Journal of Magnetic Resonance, 230, 88-97.
Olsen et al. (1995). A wavelet phase filter for emission tomography. In SPIE (vol. 2491, pp. 829-839).
Ouahabi, A. (2013). A review of wavelet denoising in medical imaging. 2013 8th International Workshop on Systems Signal Processing and Their Applications (WOSSPA), IEEE, (May 12, 2013), doi:10.1109/WOSSPA.2013.6602330, pp. 19-26.
Tisdall et al. (2005). MRI noise reduction via phase correction and wavelet-domain filtering. In Proceedings of the International Society for Magnetic Resonance in Medicine, ISMRM (vol. 5, p. 2284).
Weaver et al. (1991). Filtering noise from images with wavelet transforms. Magnetic Resonance in Medicine, 21(2), 288-295.
Zaroubi et al. (2000). Complex denoising of MR data via wavelet analysis: application for functional MRI. Magnetic resonance imaging, 18(1), 59-68.
English language abstract for CN 102800057 A (2012).
International Search Report from corresponding PCT/EP2015/000957 dated Sep. 25, 2015.

* cited by examiner

A

B

METHOD AND DEVICE FOR MAGNETIC RESONANCE IMAGING WITH IMPROVED SENSITIVITY BY NOISE REDUCTION

CROSS-REFERENCE TO RELATED APPLICATIONS

This application is a U.S. National Phase Application of PCT/EP2015/000957, filed May 8, 2015, the contents of which application is incorporated herein by reference in its entirety for all purposes.

TECHNICAL FIELD OF INVENTION

The invention relates to a method of image processing of magnetic resonance (MR) images for creating denoised MR images, in particular to a method of denoising image data in wavelet domain. A magnetic resonance imaging device for implementing the method is also disclosed. Applications of the invention are available in all fields of magnetic resonance imaging, in particular functional and/or quantitative medical imaging.

TECHNICAL BACKGROUND

For describing the background of the invention, particular reference is made to the following publications:
[1] V. R. Fuchs et al. in "Health Aff." 20: 30-42 (2001);
[2] D. I. Hoult. Sensitivity of the NMR experiment. In: D. M. Grant, R. K. Harris (eds.); Encyclopedia of Nuclear Magnetic Resonance, Vol. 7, pp. 4256-4266, Wiley, Chichester (1996);
[3] S. Zaroubi et al. in "Magn. Reson. Imaging" 18: 59-68 (2000);
[4] J. B. Weaver et al. in "Magn. Reson. Med." 21: 288-295 (1991);
[5] U.S. Pat. No. 6,741,739 B1;
[6] S. G. Chang et al. in "IEEE Trans. Image Proc." 9: 1522-1531 (2000);
[7] C. S. Anand et al. in "Magn. Reson. Imaging" 28: 842-861 (2010);
[8] US 2014/0212015 A1;
[9] E. T. Olsen et al. in "Proc. SPIE 2491, Wavelet Applications II" 829-839 (1995);
[10] R. M. Henkelman et al. in "Med. Phys." 12: 232-233 (1985);
[11] A. J. den Dekker et al. in "Phys. Medica" 30: 725-741 (2014); and
[12] D. K. Müller et al. in "J. Magn. Reson." 230: 88-97 (2013).

Magnetic resonance imaging (MRI) is a standard biomedical imaging modality and has been considered (together with computed tomography) "the most important medical innovation" during the past decades in a 2001 survey among leading US American physicians [1]. However, MRI has also an inherently low sensitivity: Considering three-dimensional (3D) proton ($^1$H) MRI of the human brain with a nominal isotropic resolution of 1 mm and at a typical static magnetic field strength of $B_0$=1.5 T used in diagnostic MRI, the individual contribution from a single image voxel (i.e., a volume of 1 µl) to the signal amplitude is of the order of only 10 nV [2]. Thus, despite its success, MRI is often limited by a low signal-to-noise ratio (SNR). The problem of an inherently low sensitivity is becoming increasingly important when applying MRI techniques, in which a certain preparation of the spin system and spatial encoding by the imaging pulse sequence is used to achieve a quantitative parametric characterization of the object under investigation (e.g., a tissue or an organ or a whole organism). Quantitative MRI (qMRI) aims to derive voxel-by-voxel well-defined biophysical, biochemical, or physiological parameters from MR images or 3D MR data sets instead of merely examining them by visual inspection. Here, the image intensity is often reduced to a very low level, which is, however, mandatory in order to retrieve the quantitative information. Examples of (semi-)quantitative mapping approaches include relaxographic imaging, quantitative magnetization transfer imaging (qMTI), diffusion-weighted imaging (dMRI), arterial spin labeling (ASL) or dynamic susceptibility contrast (DSC) imaging, for mapping tissue perfusion, or vascular space occupancy (VASO) for mapping tissue blood volume. Similarly, functional MRI (fMRI) of the brain aims at the detection of dynamic signal changes (e.g., expressed as percent of a baseline level) related to neuronal activation upon application of a stimulus or performance of a task.

To address limitations of the low SNR in magnetic resonance, several strategies are being employed for improving the signal amplitude, such as the use of higher static magnetic fields or hyperpolarization techniques. However, such strategies are demanding and expensive regarding the necessary hardware. Furthermore, the gain achieved by a higher magnetic field is only moderate (approximately linear increase with $B_0$) whereas the applicability of hyperpolarization is rather limited to specific applications. Alternatively and additionally the SNR can be improved by reducing the image noise, for example, by using improved radiofrequency (RF) receivers designed as an array of small individual coils. Appropriate choice of the size of the array elements reduces the effective size of that part of the sample that acts as a noise source, which is, however, limited by the overall size of the object to be imaged.

Besides hardware solutions for improved SNR, noise in the final image can be reduced through averaging, that is, the repetitive measurement of the data under identical conditions and subsequently co-adding them. The SNR gain results from a linear buildup of the (coherent) signal (subsequently also referred to as 'information') with the number of averages, $M_{av}$, whereas random noise only grows proportional to $\sqrt{M_{av}}$; hence, SNR improves with $\sqrt{M_{av}}$. This method requires an identical contrast for all images that are supposed to be averaged and is time consuming (e.g., to double the SNR requires four times the number of scans). In particular, while averaging of all data, e. g. from an image series acquired with variation of specific acquisition parameters to extract a quantitative property of the tissue after application of a fitting procedure, would lead to a final dataset with high SNR, it would—at the same time—destroy all underlying information about the parameter to be extracted or the time-dependence of the dynamic experiment, and hence, traditional averaging has substantial limitations. Similarly, smoothing of the images unavoidable leads to a smearing of contrast and thus effectively reduces the image resolution.

While averaging does not involve further manipulation of the acquired data than a simple voxel-by-voxel summation and division by $M_{av}$ to normalize to a constant signal level, another class of methods aims at reducing the noise by application of digital filters. Here, some contributions to an image are identified as originating from noise through the application of suitable filtering techniques and are subsequently removed or reduced. This procedure is synonymously called 'noise filtering', 'noise suppression', or 'denoising'. In many of these denoising methods, images are expanded in a functional basis that maintains their phase and amplitude distribution. By using a suitable functional basis, it is often possible to distinguish between the various contributions to the MRI data and to filter the noise [3]. Particular examples of denoising methods, which are also suitable to imaging in general, employ the discrete wavelet transform [4]. Since then, a plethora of algorithms for the adaptation of wavelet-based denoising to MRI have been proposed.

Common methods for denoising in MRI employing wavelets are based on thresholding with a range of specific modifications and adaptations. Thresholding is typically performed in a way that parts of the image are assumed to contain only (or mostly) noise, for example, based on criteria of a low image intensity and/or characteristic high-frequency fluctuations. Such parts are then set to zero to effectively remove noise [5, 6]. More advanced methods comprise spatially-adaptive or phase-adaptive thresholding [7-9], for example, to better deal with spatial variations in image intensity. Such variations may occur in images reconstructed from multi-channel array coils.

A substantial disadvantage of these approaches is the suppression of information that result from weak and fine details of the imaged object that are hidden by overlaying noise contributions and, hence, misclassified as noise. Thresholding techniques typically aim at smooth images with intact sharp edges characterizing the object, and maximum SNR, which may come at the cost of a partial loss of finer details.

Objective of the Invention

The objective of the invention is to provide an improved method of image processing of MR images, which avoids disadvantages of conventional techniques. In particular, the objective of the invention is to provide the method of image processing for denoising MR images with increased sensitivity, improved SNR and/or reduced loss of information contributions included in the MR images. Furthermore, the objective of the invention is to provide an improved MRI device being configured for creating a sequence of MR images of an object under investigation, which avoids disadvantages of conventional MRI techniques.

SUMMARY OF THE INVENTION

These objectives are solved with a method of image processing for denoising MR images and an MRI device comprising the features of the independent claims, respectively. Preferred embodiments and applications of the invention are defined in the dependent claims.

According to a first general aspect of the invention, the above objective is solved by a method of image processing of MR images for creating denoised MR images, comprising the steps of providing image data sets including multiple complex MR images, subjecting the MR images to a wavelet decomposition for creating coefficient data sets of wavelet coefficients which represent the MR images in a wavelet frequency domain (wavelet space), denoising the coefficient data sets in the wavelet frequency domain, and subjecting the denoised coefficient data sets to a wavelet reconstruction for providing the denoised MR images to be obtained.

According to the invention, the denoising of the coefficient data sets is obtained by the following steps conducted on the data in the wavelet frequency domain. A statistical amplitude processing is provided wherein normalized coefficient data sets of wavelet coefficients are calculated by normalizing the coefficient data sets with a quantitative amount of variation of noise contributions included in the coefficient data sets. The quantitative amount of variation is a quantitative statistical measure of the noise contributions, preferably the standard deviation or another measure related to the standard deviation, like the variance. Furthermore, statistical phase processing is provided wherein the wavelet coefficients of each coefficient data set are averaged for providing averaged wavelet coefficients of the coefficient data sets, and phase difference maps are calculated for all coefficient data sets, wherein the phase difference maps provide phase differences between the phase of each wavelet coefficient and the phase of the averaged wavelet coefficients. Subsequently, scaled averaged coefficient data sets of wavelet coefficients are calculated by scaling the averaged wavelet coefficients with scaling factors, which are obtained by comparing parts of the normalized wavelet coefficients of the normalized coefficient data sets that are in phase with the averaged wavelet coefficients. Rescaled coefficient data sets of wavelet coefficients are calculated by applying a transfer function (or: lookup table) on the coefficient data sets and applying the transfer function on the scaled averaged coefficient data sets, wherein the transfer function includes combined amplitude and phase filters, each depending on the normalized coefficient data sets and the phase difference maps, resp. Applying the transfer function comprises a multiplication of the wavelet coefficients with the transfer function, resulting in a rescaling of the wavelet coefficients. Applying the transfer function on the scaled averaged coefficient data sets is constructed such that noisy wavelet coefficients are replaced by scaled averaged wavelet coefficients carrying signal contributions. Thus, as a main advantage of the invention, less signal contributions are lost than with the conventional threshold technique. Finally the wavelet reconstruction is applied on the rescaled coefficient data sets for providing the denoised MR images.

It is an inherent characteristic of MRI to measure complex data in k-space, that is, data consisting of a real and an imaginary part. From these complex k-space data, complex images are reconstructed, which may be presented as separate magnitude (amplitude) and phase images. Most often, however, only the amplitude part is displayed, in particular on conventional clinical MRI scanners, and the phase part is discarded. On the contrary, according to the invention, which is referred to as "Adaptive Wavelet-based Enhancement of Signal Over Multiple Experiments" (AWESOME), the phase part is explicitly included in the data processing for using its distinct features to achieve improved image quality while avoiding shortcomings of existing denoising techniques.

Advantageously, while conventional thresholding methods are implemented in a way to balance achievable SNR improvement and loss of image details, the inventive method permits to recover details hidden by noise in the original image rather than deleting them in the process of denoising. This is achieved by an adaptive averaging over image data sets each of an individual measurement, however without the need of repeated acquisitions of images under identical conditions. It is thus most favorable in applications, in which repeated scanning is inherently conducted. Examples of such experiments may include parameter variations in order to obtain maps of quantitative biophysical, biochemical, or physiological parameters by fitting an image series voxel-by-voxel or in a pre-defined region of interest (ROI) to an underlying model (e.g., in relaxography, qMTI, dMRI) or in cases, where the fluctuations of the system are observed as a function of time (e.g., in ASL or in fMRI).

The principle of the method of the invention lies in between averaging and thresholding in the wavelet space. In conventional thresholding, the data are classified as either containing primarily noise (e.g., if the intensity is below a certain threshold) or containing primarily meaningful information (if the intensity is above the threshold). In the method of the invention, however, the noise class is not simply zeroed, but it undergoes the averaging and scaling procedure.

A particular property of the wavelet decomposition/reconstruction is the consistency of signal phase. This leads to the advantage that signal phase coherence is preserved in wavelet space in the same way as it is observed in image space [10], which can be exploited for classifying contributions from information and those from noise. Advantageously, the averaging property of the method of the invention leads to a noise level proportional to $\sqrt{M}$ when combining data from M individual experiments as obtained for regular averaging. Additionally, it also avoids loss of subtle signal contributions that might have been misclassified or simply hidden under the noise floor as these contributions build up proportional to M due to their phase coherence. The intensity in wavelet space obtained after the averaging step is resealed, whereby the scaling factor is derived from the phase-coherent contribution to the averaged wavelet coefficients and the transfer function. The transfer function considers the statistical properties of the noise and meaningful coefficients. In the simplest (and ideal) case, where only contributions from random noise are present, this may be characterized as a uniform noise distribution. While the rescaling can only have a finite accuracy, it is less destructive than the simple removal of entire parts of the coefficient image as done in thresholding.

According to a preferred embodiment of the invention, the step of providing the image data sets of multiple complex MR images includes providing a series of MR image raw data and calculating a quantitative amount of variation of the phase of signal contributions in the MR image raw data. The term MR image raw data in this context (and hereafter) refers to the image space (or frequency domain), and is used to indicate image data to which the inventive denoising procedure has not been applied so far. The quantitative amount of variation is a quantitative statistical measure of the signal contributions, preferably the standard deviation or another measure related to the standard deviation, like the variance. Accordingly, the image data sets of multiple complex MR images include the noisy raw image data and the quantitative amount of variation, like the standard deviation, of the phase of signal contributions therein. The MR image raw data are provided in k-space or in time space. The series of MR image raw data is delivered to a processor conducting the inventive method directly by an MRI device or from a distant resource via data communication means. Advantageously, the quantitative amount of variation, in particular the standard deviation, of the phase of signal contributions in the MR image raw data can be used for constructing the transfer function.

Generally, the series of MR image raw data represents at least two MR images. With preferred applications of the invention, larger numbers of MR images are collected, e. g. at least 4, preferably at least 10.

Preferably, the step of providing the image data sets of multiple complex MR images further includes a spatial registration of the MR image raw data and/or a phase correction of the MR image raw data for compensating a consistent time evolution over the series of MR image raw data related to a collection of the MR image raw data.

According to a further preferred embodiment of the invention, the amplitude and phase filters included in the transfer function are constructed on the basis of sigmoid functions and the quantitative amount of variation, in particular the standard deviation, of the phase of signal contributions in the MR image raw data.

While the phase is preserved in wavelet space, the sign of a signal contribution from a detail in image space may flip the phase in wavelet space by an increment of rt. Therefore, according to a further preferred embodiment of the invention the phase filter included in the transfer function comprises mirrored phase dependent portions.

Advantageously, the transfer function can be constructed based on additional image information, e. g., from reference images and/or prior knowledge about noise contributions. In particular, the determination of the transfer function can be improved by exploiting prior knowledge about the underlying noise statistics and the corresponding coefficients. Such information may be gained from separate measurements (e.g., in medical imaging with reference scans in one or more healthy volunteers with otherwise identical imaging protocol parameters but a sufficient number of repetitions). These repetitive reference scans may be used to achieve a high SNR by traditional averaging or extract reliable information on the statistical properties of the data. The information from such selected scans is then fed into an optimization routine for optimizing the transfer function to obtain a refined method of the invention procedure with improved performance.

According to a further preferred embodiment of the invention, the standard deviation of noise contributions included in the coefficient data sets is calculated by the steps of calculating a standard deviation of the absolute wavelet coefficients, separating of noise-containing and information-containing coefficients by applying a mask depending on the standard deviation, and calculating the standard deviation of the noise-containing coefficients.

Advantageously, the noise-containing coefficients can be subjected to a statistical analysis for obtaining a distribution of intensity and phase of the noise-containing coefficients and a potential correlation of the noise over the image series. Resealed coefficient data sets of wavelet coefficients can be calculated with improved details of signal contributions if according to a further preferred embodiment of the invention the transfer function is constructed in dependency on the distribution of intensity and phase of the noise-containing coefficients.

Advantageously, the wavelet decomposition for creating the coefficient data sets of wavelet coefficients can be conducted using a wavelet base as it is known in the field of wavelet transformations. The specific choice of a wavelet may vary depending on the individual MR imaging process and/or properties of the object. Preferably, wavelets with a sufficiently large tapping width (e.g., eight or more support points) are used. Furthermore, the wavelet decomposition preferably is calculated with at least three frequency bands each including one sub-band for 1D image data, three sub-bands for 2D image data or seven sub-bands for 3D image data.

In a more general scenario, noise correlations may be present (e.g., when using multi-channel receive arrays of coil elements with partly overlapping sensitivity profiles and/or application of parallel imaging techniques) or misregistered spurious signal contributions (e.g., 'ghosting' artifacts) may be found. In such cases, the image background may not be sufficiently characterized by a purely random phase but, more appropriately, by a superposition of a random phase component (originating from to random noise) and another component that shows some degree of phase coherence with the information-containing image parts. The method of the invention is capable to suppress such nuisance contributions, which is equivalent to the attempt to suppress purely random noise in the ideal case. To emphasize this equivalence, the image background consisting of a superposition of a random and a partially coherent phase component is referred to as "correlated noise". To account for the presence of correlated noise, the transfer function can be adapted (e.g., empirically) to improve the achieved suppression of unwanted image contributions.

Furthermore, the correlated noise can be suppressed, if the step of calculating the normalized coefficient data sets of wavelet coefficients is modified such that the coefficient data sets are normalized with a sub-band specific standard deviation of noise contributions of the coefficient data sets included in the sub-bands of the wavelet decomposition, and the phase difference maps, the scaling factors and the transfer function are calculated on the basis of the sub-band specific standard deviation.

According to a second general aspect of the invention, a method of magnetic resonance imaging of an object is disclosed, comprising the steps of collecting a series of MR image raw data for obtaining multiple complex MR images, and subjecting the MR images to an image processing according to the above first aspect of the invention.

According to a third general aspect of the invention, an MRI device is disclosed, which is configured for creating a sequence of MR images of an object under investigation. The MRI device comprises an MRI scanner including a main magnetic field device, at least one radiofrequency excitation coil, magnetic field gradient coils and at least one radiofrequency receiver coil, and a control device being adapted for controlling the MRI scanner for collecting the series of sets of image data and for reconstructing the sequence of MR images with the method according to the above first aspect of the invention.

Further general subjects of the invention are a computer program residing on a computer-readable medium, with a program code which, when executed on a computer, carries out the method(s) according to the above first and/or second aspect of the invention, and/or an apparatus comprising a computer-readable storage medium containing program instructions which, when executed on a computer, carry out the method(s) according to the above first and/or second aspect of the invention.

BRIEF DESCRIPTION OF THE DRAWINGS

Further details and advantages of the invention are described in the following with reference to the attached drawings, which show in.

PREFERRED EMBODIMENTS OF THE INVENTION

Preferred embodiments of the invention are described in the following with particular reference to the mathematical formulation of the inventive denoising in wavelet space and examples of images obtained with the inventive technique. Details of an MRI device and the operation thereof, the numerical implementation of the mathematical formulation using available software tools and optional further image processing steps are not described as far as they are known from conventional MRI techniques. Furthermore, exemplary reference is made in the following to MR imaging. It is noted that the application of the invention is not restricted to MR imaging, but rather possible for denoising other complex data obtained from measurements.

Figure 1:
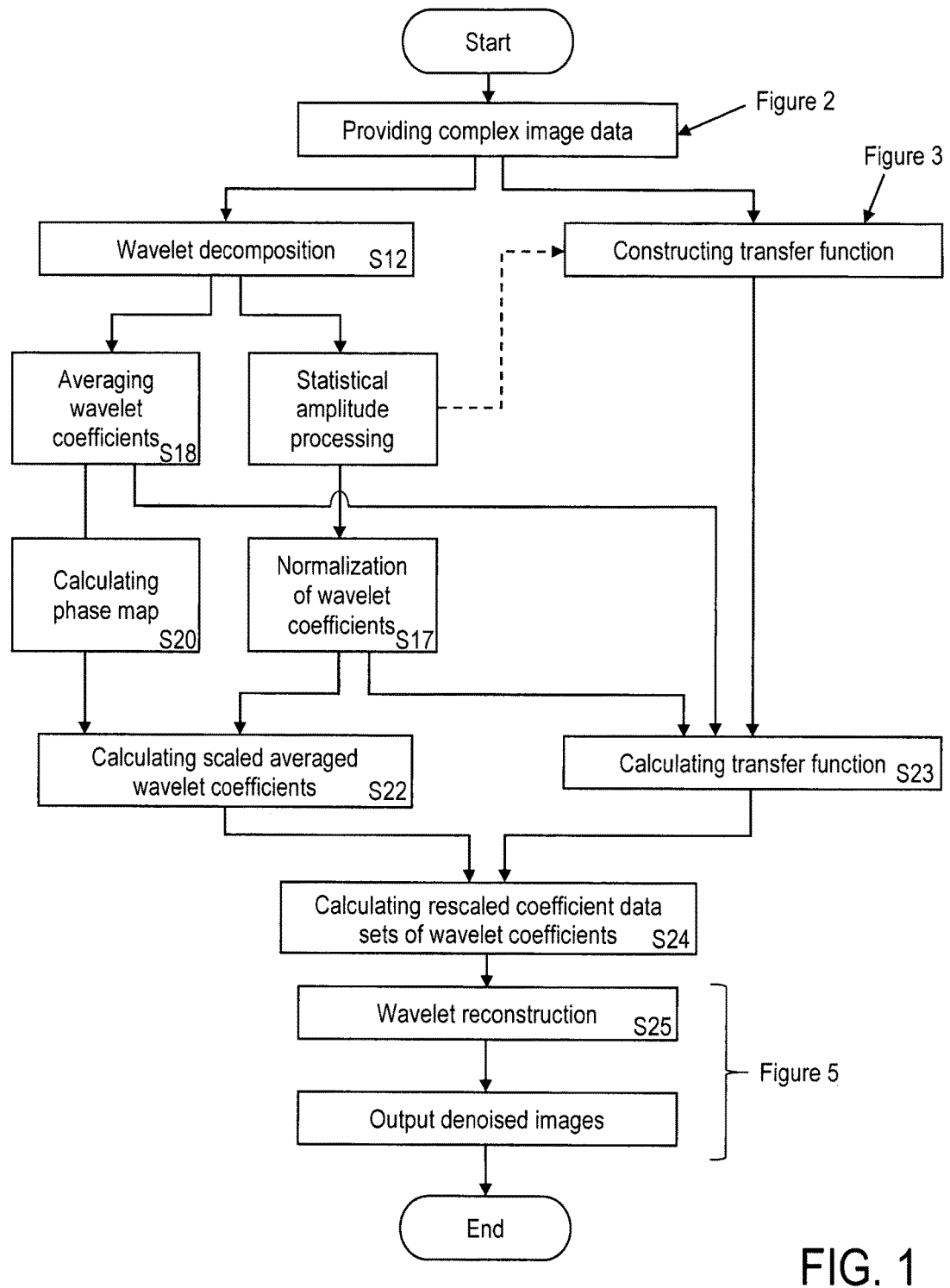
FIGS. 1 to 5: flowcharts illustrating preferred embodiments of the inventive image processing method.

A step-by-step description of the general procedure underlying the method of the invention (subsequently referred to as 'standard AWESOME') is shown in FIGS. 1 to 5 and summarized below. FIG. 1 is a general overview illustrating main steps of the inventive method. Details of the main steps are represented in FIGS. 2 to 5 as indicated in FIG. 1. The individual steps, which are indicated with S1, S2, . . . , are described in the following.

Provision of Complex Image Data

Figure 2:
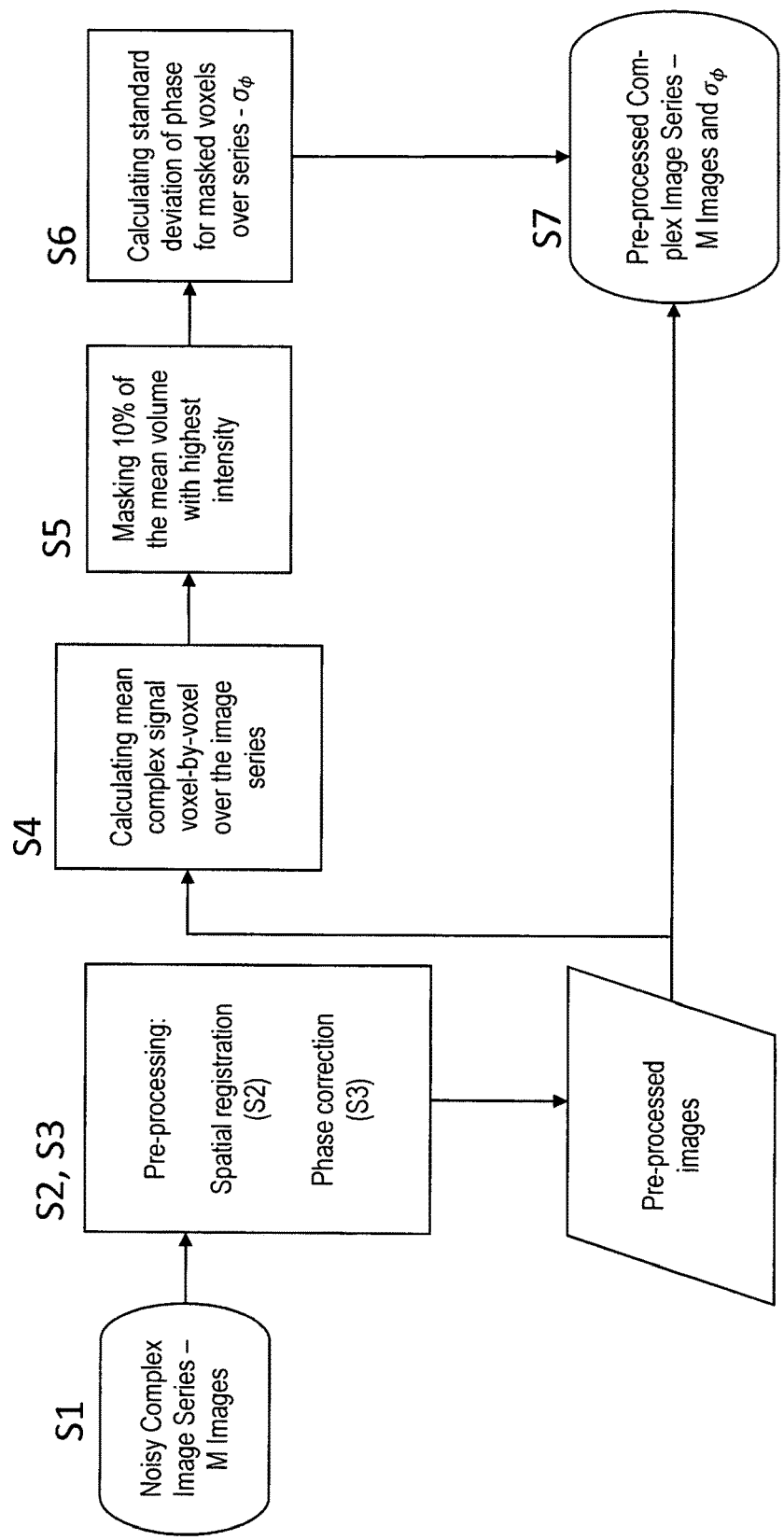

According to FIG. 1, the first step of providing complex image data comprises steps S1 to S7 as illustrated in FIG. 2. Steps S1 and S2 are routine operations, which can be applied as generally known in the field of MR image processing.

Step S1:

Initially, a series of M raw image data sets (M raw images) from the same object is provided, e. g. measured with the MRI device, as complex data with amplitude and phase as floating point numbers. Ideally, object motion should be limited, similar to general prerequisites of routine averaging in MRI. However, translational motion may also be corrected without loss of information in a pre-processing step (S2).

Step S2:

Potential misalignment of the image data (e.g., due to motion) is optionally corrected with a consistent degree of interpolation to avoid variation in the noise statistics over the image series.

Step S3:

An approximate phase correction is optionally applied in image space if the signal phase demonstrates a consistent time evolution over the image series related to the preparation of the spin system (e.g., as obtained with techniques used for $B_0$ mapping). This phase correction is performed to avoid partially destructive interference of information other than random noise during the averaging effect in the method of the invention. The phase correction has no effect on the noise statistics. The parameters of the applied correction scheme are stored in memory and used to reverse the phase manipulation after the reconstruction step (S25).

Advantageously, all voxels have a consistent phase after the phase correction. This facilitates step S5 (see below) being reduced to calculating the standard deviation of the masked voxels only. Furthermore, a smooth phase characteristic is obtained in the object, so that a misinterpretation of phase oscillations in the object domain as a structure in wavelet domain is avoided.

Step S4:

The mean signal intensity (in image space) over the image series is computed voxel-by-voxel.

Step S5:

A mask is generated that contains the voxels with the highest mean signal intensity as a representative sample for statistical evaluation. The percentage of voxels included in this mask, selected e. g. in a range of 5% to 15%) may vary depending on the resolution and total number of images in the series in order to achieve a good balance between sufficiently fast calculations and reliable/representative results. It is noted that steps S4 and S5 are routine operations, which can be applied as generally known in the field of MR image processing.

Step S6:

Calculation of the standard deviation, $\sigma_\phi$, of the phase of masked voxels in the image series. As the phase is preserved in the wavelet decomposition, knowledge of the expected phase variation of signal contributions other than noise (i.e., containing information) can be used for the classification of wavelet coefficients as being either meaningful (i.e., containing information) or noise. Alternatively, another quantitative statistical measure of the phase of masked voxels in the image series can be calculated instead of the standard deviation.

Step S7:

The image data sets including the multiple complex MR images (pre-processed complex image data) and $\sigma_\phi$ are passed over to a processing pipeline operating in the wavelet domain. Unless noted otherwise, all subsequent steps are being performed after a discrete wavelet transform (S12). Following standard practice, data in wavelet space are henceforth referred to as 'coefficients'.

Constructing the Transfer Function

Figure 3:
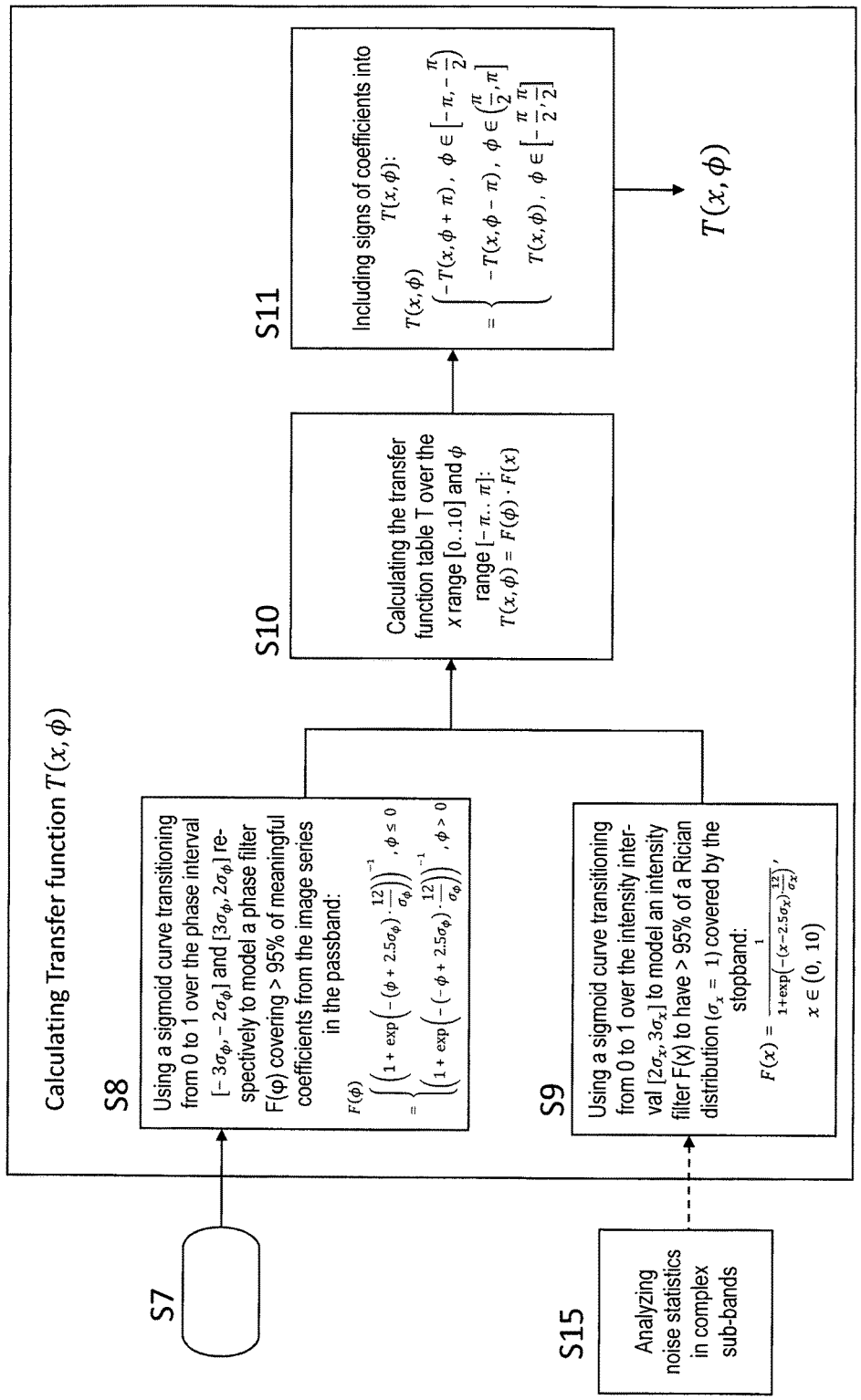
Figure 4:
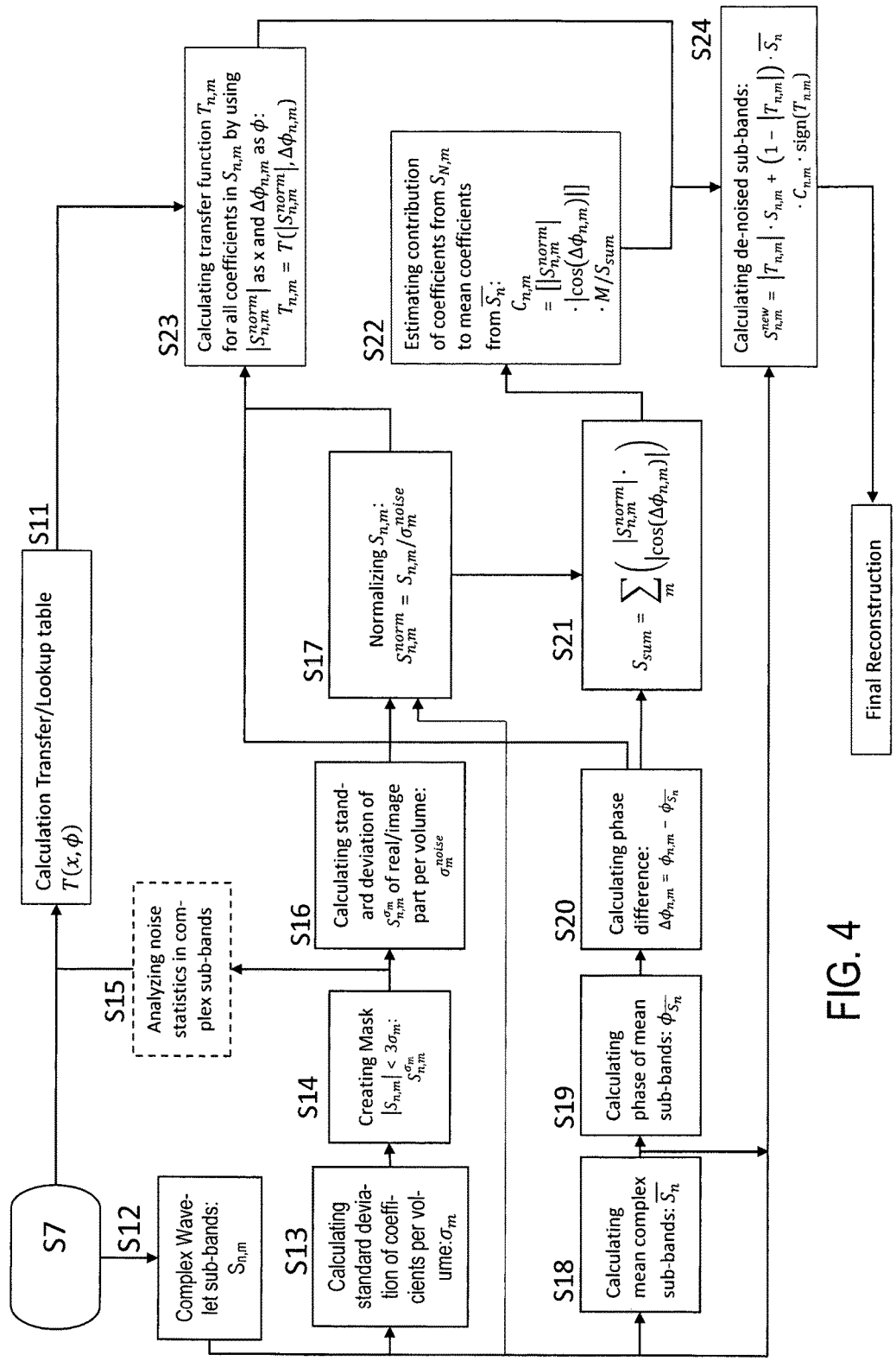
Figure 5:
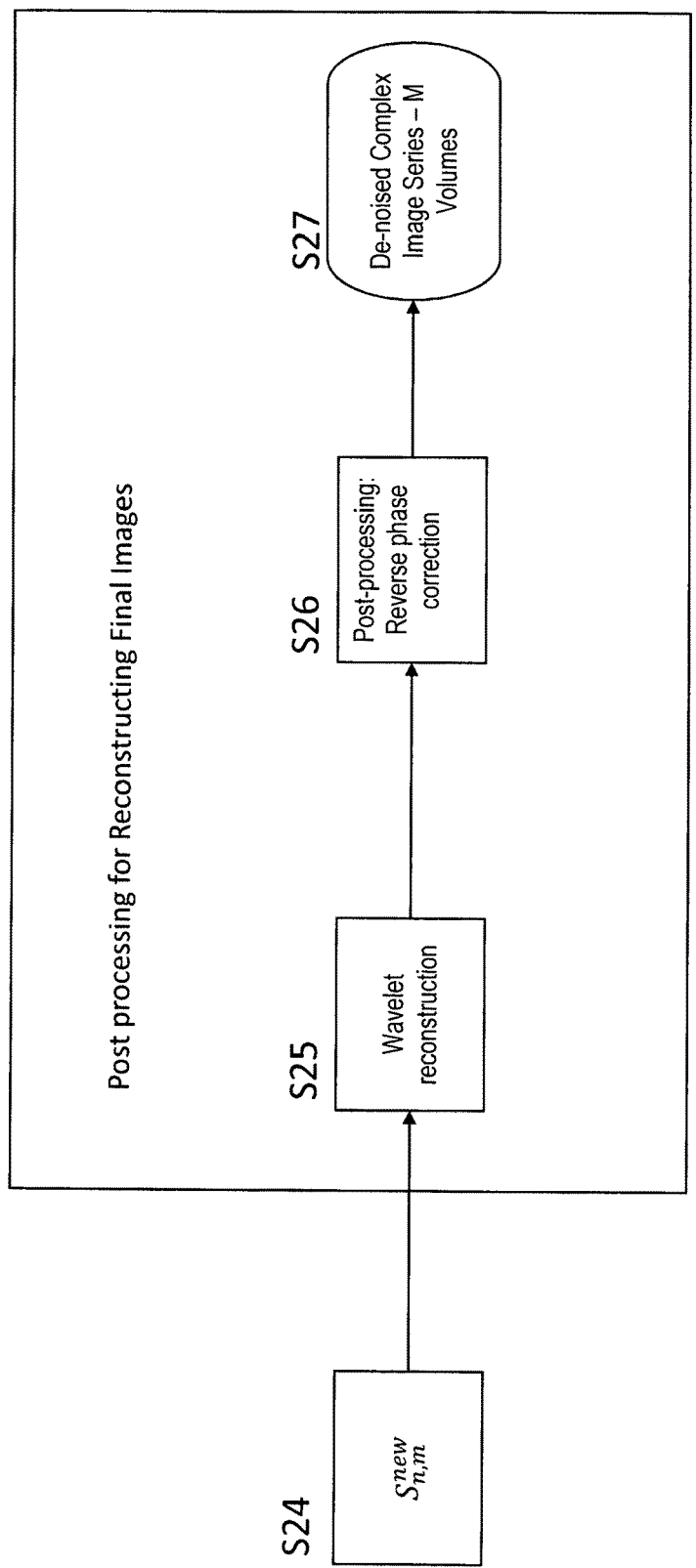

According to FIG. 1, the standard deviation, $\sigma_\phi$, of the signal contributions in the MR images is used for constructing the transfer function with steps S8 to S11 as illustrated in FIG. 3.

Step S8:

A phase filter is created based on a monotonous continuous function, using the standard deviation, $\sigma_\phi$, of the signal contributions in the MR images. Examples of suitable functions include a logistic function or a similar sigmoid curve, $f(x)$. A particular characteristic of a suitable function is a smooth transition between noise represented by 0 in the stopband, and information represented by 1 in the passband. The example of a logistic function is given by $$f(x, x_0, k) = \frac{L}{1 + e^{-k(x-x_0)}} \quad (1)$$

where $x_0$ is the midpoint, L the maximum value, and k the steepness of the curve. A choice of L=1 is used to obtain a transition from 0 to 1.

Figure 6:
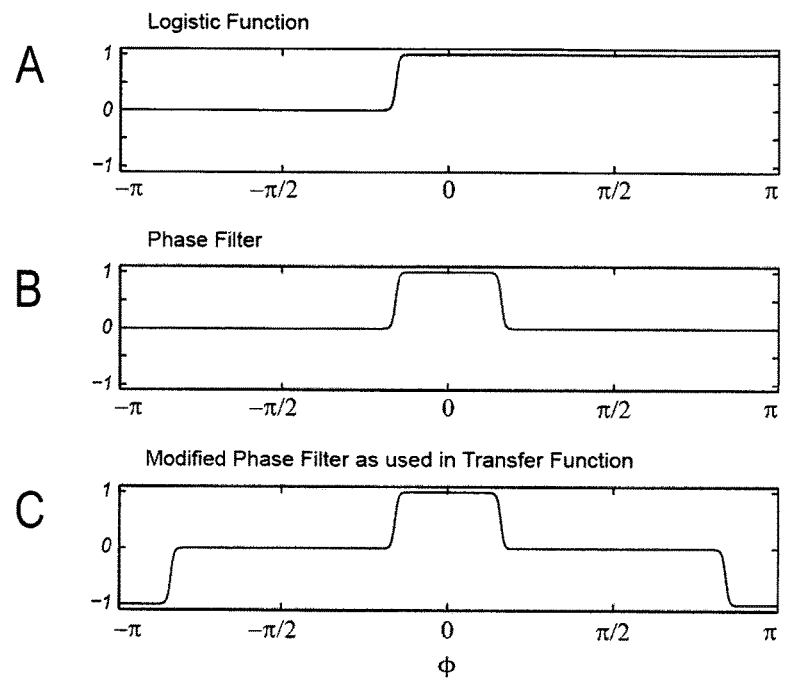
FIG. 6: a schematic illustration of a transfer function.

FIG. 6A illustrates the logistic function $f(x, x_0, k)$ according to Eq. (1) with x=$\phi$, $x_0$=2.5 $\sigma_\phi$, k=12/$\sigma_\phi$, L=1, and $\sigma_\phi$=0.2. The phase filter, F($\phi$), derived from $f(\phi, 2.5\sigma_\phi, 12/\sigma_\phi)$ is shown in FIG. 6B. The phase filter is set to F($\phi\leq0$)=$f(\phi, 2.5\sigma_\phi, 12/\sigma_\phi)$ and to F($\phi\leq0$)=$f(-\phi, 2.5\sigma_\phi, 12/\sigma_\phi)$. It is used to distinguish information from noise via their phase. Here, midpoints are set to $\phi$=±2.5$\sigma_\phi$ on the phase axis, and the width is adjusted to obtain a (sigmoid) transition from 0 to 1 in the interval [−3$\sigma_\phi$, −2$\sigma_\phi$] and a transition from 1 to 0 in the interval [+2$\sigma_\phi$, +3$\sigma_\phi$]. This achieves that >95% of all signal contributions containing information are inside the passband of the filter. FIG. 6C illustrates a modified phase filter, obtained by mirroring F($\phi$) at $\phi$=$\pi$/2 and at $\phi$=−$\pi$/2 and subsequently inverting the sign for $\phi$>$\pi$/2 and for <−$\pi$/2.

The application of the invention is not restricted to the above particular transfer function. Other transfer function can be constructed using the phase of the complex coefficients for a decision whether a coefficient belongs to noise or signal contributions. While the parameters of the above logistic function are determined on the basis of the standard deviation of the phase of intense signal contributions in image domain, other filter functions can be used, e. g. empirically determined filter functions or a logistic function with L<1. As a further modification, the amplitude of the image data could be used in addition to the phase of the image data for determining the parameters of the phase filter.

Step S9:

A similar amplitude filter F(x) is calculated for an arbitrary signal amplitude axis of range x∈[0,10] and standard deviation $\sigma_x$=1. The amplitude filter F(x) is calculated on the basis of the masked signal contributions obtained in step S14 and optionally based on the statistical analysis of the masked noise-containing coefficients in step S15. The (sigmoid) transition for this amplitude filter from 0 (equivalent to the assumption of pure noise) to 1 (equivalent to the assumption of pure information) occurs in the interval [2$\sigma_x$, 3$\sigma_x$] by setting the filter's midpoint to $x_0$=2.5$\sigma_x$—similar to the choice for the phase filter. In subsequent step S17 the wavelet decomposition of each image will be normalized to obtain $\sigma_x$=1. We note that the same filter may be used for either complex-valued data or absolute-valued data. If absolute-valued data are processed, previously complex Gaussian noise becomes Rician noise [11, 12] and more than 95% of the noise amplitude are inside the stopband of the filter.

Corresponding to step S8, the goal is to use the amplitudes of the complex coefficients for a decision whether a coefficient belongs to noise or signal contributions. Other filter functions can be used as mentioned with reference to step S8.

Step S10:

For easier implementation, a two-dimensional (2D) filter is calculated from both filters, and is subsequently referred to as the 'transfer function':

$$T(x,\phi)=F(x)F(\phi). \quad (2)$$

This transfer function is employed to decide whether or not data from the averaged wavelet decomposition are transferred into the original wavelet decompositions.

In (2), the filter criteria of the phases and amplitudes are combined in a filter function. The use of the product is not mandatory, other functional relationships are possible if they have a corresponding filter characteristic. The transfer function can also be a general function that does not consist of separate phase and amplitude filtering.

Step S11:

As already stated, phase is preserved in wavelet space. However, the phase of the complex signal obtained by the wavelet transformation may change by ±π, depending on the signal amplitude. Thus, the sign of a signal contribution from a detail in image space may flip the phase in wavelet space by an increment of π. To account for this effect, the transfer function is modified by mirroring the phase filter at =π/2 and $\phi$=−π/2 and inverted in sign for $\phi$>π/2 and $\phi$<−π/2 (see FIG. 6c). This modification permits identification of information content flipped by π in phase in the wavelet space by use of the transfer function.

Denoising in Wavelet Space

The MR images obtained in step S7 are subjected to a wavelet decomposition (step S12) for creating coefficient data sets of wavelet coefficients representing the MR images in the wavelet frequency domain. As shown in FIG. 1, the coefficient data sets of wavelet coefficients are subjected to statistical amplitude and phase processing steps, including calculating normalized wavelet coefficients and a phase map, which are used for calculating (adapting) the transfer function on the basis of the present coefficient data sets and for rescaling the wavelet coefficients. The associated steps S12 to S24 are illustrated with further details in FIG. 4.

Step S12:

The wavelet decomposition is a routine operation, which can be applied as generally known in the field of data processing, in particular in medical image processing. The choice of parameters can follow the specifications as described in standard literature and textbooks. In particular, for each pre-processed complex individual image data set, m, from a total of M data sets in the series, its complex wavelet decomposition is calculated with p≥3 frequency bands. Each of the p frequency bands is further subdivided into q sub-bands depending on the (spatial) dimensionality of the input data (i.e, q=1, 3, or 7 for one-dimensional (1D), 2D, or 3D input data, respectively) yielding a total of N=pq sub-bands, $S_{n,m}$ with n=1, ..., N, for each of the individual image data sets. The choice of p≥3 has advantages in terms of achieving already a good separation of noise from information based on the (typically fulfilled) assumption that noise is characterized by high frequencies.

Step S13:

The standard deviation of the absolute coefficients, $\sigma_m$, is computed for each data set.

Step S14:

Subsequently, a mask is generated from all coefficients smaller than $3\sigma_m$ to obtain a rough separation of predominantly noise-containing and predominantly information-containing coefficients. The selected factor 3 is not mandatory, but may be selected within a reasonable range depending on the imaging conditions.

Step S15:

A statistical analysis of the masked noise-containing coefficients for each data set can be performed. In particular, the distribution of intensity and phase is calculated as well as a potential correlation of the noise (i.e., a deviation from a uniform phase distribution for the noise-containing coefficients) over the image series. This effect might cause a constructive interference of the noise upon averaging and may be removed by a baseline correction in an additional post-processing step if necessary. Furthermore, the result of the statistical analysis in step S15 can be used for constructing the transfer function in steps S8 to S11.

Step S16:

Standard deviations of the real and imaginary parts of the masked coefficients for each data set are computed and their average is used as the standard deviation of the noise for each data set, $\sigma_m^{noise}$.

Step S17:

The wavelet decompositions of each data set are normalized with the standard deviation; of the noise, $\sigma_m^{noise}$:

$$S_{n,m}^{norm} = \frac{S_{n,m}}{\sigma_m^{noise}}. \quad (3)$$

The absolute value of the normalized decompositions will be used in steps S21 and S22 to provide intensity information to the transfer function. Alternatively, the normalization can be done using another quantitative statistical measure of the noise contributions.

Step S18:

Averaged complex coefficients (mean over the image series) $\overline{S_n}$ are computed. In each averaged coefficient, the intensity of noisy coefficients is reduced by a factor of $\sqrt{M}$ or less depending on the amount of information contributing to the specific coefficient over the image series. It is noted that image reconstruction from the resulting averaged wavelet decomposition would produce a result that is equivalent to simple averaging of the image series in image space.

Step S19:

Phase maps, $\phi_{\overline{S_n}}$, are extracted for all averaged sub-bands.

Step S20:

Phase difference maps are calculated for all coefficients of the individual data sets using the previously computed phase maps according to:

$$\Delta\phi_{n,m} = \phi_{n,m} - \phi_{\overline{S_n}}. \quad (4)$$

These phase difference maps are subsequently used to provide phase information to the transfer function.

Step S21:

The phase difference maps and the normalized wavelet decompositions are used to sum up intensity contributions that are in phase with the mean coefficients. The contribution of each coefficient can be scaled by the phase difference between a coefficient and the associated averaged coefficient by a continuous function. This continuous function should be designed according to the rules that phase-coherent coefficients are scaled by 1 and perpendicular coefficients are scaled by 0, assuming that the limiting case of a 90° phase difference does not lead to a contribution to the averaged coefficient. As an example of a suitable function fulfilling these rules, the absolute value of the cosine of the phase difference is subsequently used, which leads to:

$$S_{sum} = \sum_m |S_{n,m}^{norm}| \times |\cos(\Delta\phi_{n,m})|. \quad (5)$$

Step S22:

Scaling coefficients $C_{n,m}$ are calculated, which are used for introducing scaled averaged coefficient data sets $\overline{S_n} \cdot C_{n,m}$ in step S24 (see below). The individual contribution from each coefficient of the series to the averaged coefficient is estimated by comparing the parts of the individual normalized coefficients that are in phase with the mean coefficients obtained by summation in step S21. For this estimation the same rules apply as described in step S21. In particular, the function used for phase-difference-dependent scaling should follow the same general rules but is not necessarily bound to the specific choice of an analytical or numeric function as used in step S21. For simplicity, the absolute value of the cosine is subsequently used in analogy to the exemplary choice in step S21. The contribution is expressed as a factor $C_{n,m}$ for each coefficient that can be used to scale the averaged coefficients to recreate the intensity of the information content of a noise-classified coefficient that constructively contributed to the averaged coefficient:

$$C_{n,m} = \frac{|S_{n,m}^{norm}| \times |\cos(\Delta\phi_{n,m})|}{S_{sum}} \times M. \quad (6)$$

Step S23:

The transfer function $T(x, \phi)$ constructed in step S11 is computed for all coefficients of all data sets by selecting $|S_{n,m}^{norm}|$ as x and $\Delta\phi_{n,m}$ as $\phi$:

$$T_{n,m}(x,\phi) = T(|S_{n,m}^{norm}|, \Delta\phi_{n,m}). \quad (7)$$

Step S24:

Scaled averaged coefficient data sets $\overline{S_n} \cdot C_{n,m}$ are calculated by scaling the averaged wavelet coefficients $\overline{S_n}$ with factors $C_{n,m}$ obtained with step S22. Coefficients in the single wavelet decompositions are replaced by rescaled averaged coefficients based on the classification of the coefficient obtained by applying the transfer function on the coefficient data sets ($S_{n,m}$) and on the scaled averaged coefficient data sets:

$$S_{n,m}^{new} = |T_{n,m}| S_{n,m} + (1-|T_{n,m}|)\overline{S_n} C_{n,m} \text{sign}(T_{n,m}), \quad (8)$$

where $S_{n,m}^{new}$ is the new wavelet coefficient for each data set containing scaled averaged data that approximately represent the information that was previously (partially) hidden by noise at positions where the transfer function did not indicate presence of information prior to averaging, and sign(x) returns the sign of the argument x.

Image Reconstruction

The denoised coefficients obtained in step S24 are subjected to a wavelet reconstruction (step S25), followed by an output of the denoised images, as shown in FIG. 1. The final processing for the output of the denoised images may include further steps, which are illustrated with details in FIG. 5.

Step S25:

Wavelet reconstruction of the $S_{n,m}^{new}$ is performed to reconstruct de-noised image data of the series preserving strong details (e.g., sharp edges) and also recovering details that were indistinguishable from noise in the original image series. Again, the wavelet reconstruction is a routine operation, which can be applied as generally known in the field of data processing.

Step S26:

The phase-correction procedure of step S3 is reversed to regenerate a signal phase consistent with the input data.

Step S27:

The improved image series is stored in memory or otherwise processed, e. g. recorded, printed or provided for further image analysis.

Alternative Embodiment

In order to better deal with the occurrence of correlated noise as defined above, a number of steps in the 'standard AWESOME' procedure are optionally modified to obtain an improved version (also referred to as 'refined AWESOME') that achieves suppression of spurious signal contributions to the background intensity besides those from purely random noise. In particular, the steps S16 and S17 are modified and steps S20 to S23 are replaced by the alternative steps S20A to S23A, respectively, as detailed below. The other steps of 'standard AWESOME' remain unchanged in 'refined AWESOME'.

The modified embodiment is based on the following considerations of the inventors. Firstly, the average intensity of spurious signal correlates to some degree with the average signal intensity in the preselected mask (i.e., the 10% voxels with the highest mean signal intensity) whereas the average level of uncorrelated random noise is independent of the average signal intensity. Consequently, uncorrelated random noise will be the dominant source of unwanted intensity in images of relatively low signal whereas spurious signal will be the dominant contribution to unwanted signal in images of sufficiently high signal intensity. Secondly, the spurious signal will show some degree of phase coherence with the signal phase in the preselected mask, which is not the case for uncorrelated random noise characterized by a uniformly distributed phase.

Due to partial phase coherence of the spurious signal, the application of the cosine of the phase difference, $\cos(\Delta\phi_{n,m})$, according to steps S20 to S22 becomes less effective. To address the variation of noise intensity, a sub-band-specific standard deviation of the noise, $\sigma_{n,m}^{noise}$, is computed consistent with steps S16 and S17 instead of a single $\sigma_{n,m}^{noise}$ representing the standard deviation of the noise for the entire wavelet decomposition of each image data set m. These sub-band-specific standard deviations are used to modify steps S20 to S23 according to:

Step S20A: An alternative option to compute phase difference maps is given by:

$$\Delta\psi_n = \phi_{S_{sum}} - \phi_{\overline{S}}, \quad (9)$$

where $\phi_{S_{sum}}$ is the phase of a non-scaled coefficient sum, which will be described in step S21A and $\phi_{\overline{S}}$, is obtained from step S19.

Step S21A: The phase of the non-scaled coefficient sum introduced in step S20A is computed by:

$$\phi_{S_{sum}} = \arg(S'_{sum}) \text{ with } S'_{sum} = \sum_m S_{n,m}^{norm} = \sum_m \frac{S_{n,m}}{\sigma_{n,m}^{noise}}, \quad (10)$$

where arg(x) operating on a complex number x yields the angle between the line joining the point to the origin in the complex plane and the positive real axis.

Step S22A: A modified contribution factor is calculated using the alternative phase difference introduced in step S20A according to:

$$C'_{n,m} = \frac{|S_{n,m}^{norm}| \times \cos(\Delta\phi_n)}{S'_{sum}} \times M \times c_{corr}, \quad (11)$$

where $c_{corr}$ is an empirically determined correction constant that is introduced to avoid overestimation of coefficients due to the lack of additional scaling in the non-scaled coefficient sum from Equation (19) in step S21A. A reasonable choice for the correction constant is, for example, $c_{corr}=0.95$.

Step S23A: The phase difference from the non-scaled coefficient sum and the averaged coefficients $\Delta\phi_n$ are used for the computation of a modified transfer function, $T'_{n,m}(x, \phi)$:

$$T'_{n,m}(x,\phi) = T(|S_{n,m}^{norm}|, \Delta\phi_n). \quad (12)$$

The transfer function may be further modified by defining an arbitrary number $\xi$ of sub-functions (e.g., $\xi=10$) that are concatenated. Each of these sub-functions act on an specific interval $i=1, \ldots, \xi$ along the $|S_{n,m}^{norm}|$ axis and are characterized by an individually adapted width of the corresponding phase filter, $\Delta\phi_n^i$, that is applied in this interval. This modification is particularly useful if prior knowledge is available to optimize the variation of $\Delta\phi_n^i$ in the specific intervals. This modification is performed to achieve an improved classification of coefficients to distinguish 'noise' and 'information'. In particular, the width of the passband of the phase filter according to step S8 is reduced for smaller coefficients, which better addresses the problem of residual phase correlation in the case of correlated noise. Similarly to narrowing the passband for small coefficients, a widening of the passband for larger coefficients is performed based on the assumption that these coefficients are dominated by contributions from 'information', which ideally should remain unchanged upon application of the method of the invention. If correlated noise due to spurious background signal is present, the average phase estimated in step S19 may be partially corrupted, which might introduce offsets in the estimated phase differences according to steps S20 or S20A and, hence, affect the calculation of factors $C_{n,m}$ or $C'_{n,m}$ in steps S22 or S22A, respectively. This more conservative selection of the passbands for large coefficients avoids potential loss of meaningful information, which might be caused by an artificial phase offset introduced by the presence of correlated noise. Finally, the intensity filter may be adjusted to avoid unwanted overlap of the stopband of the (modified) phase filter with the intensity filter's stopband at low intensities.

Examples of Application

Figure 7:
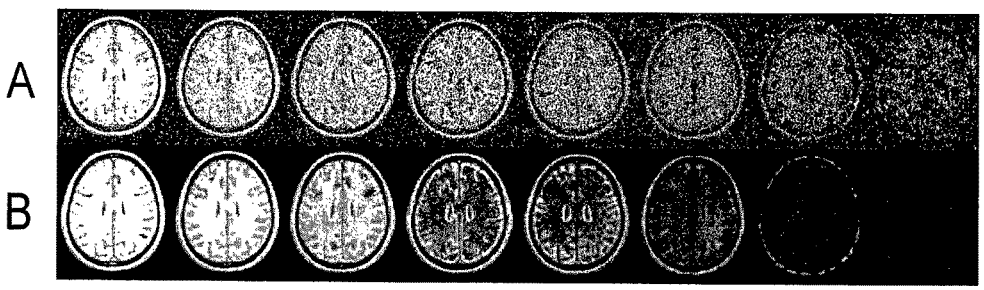
FIGS. 7 to 13: illustrations of applications of the invention.
Figure 8:
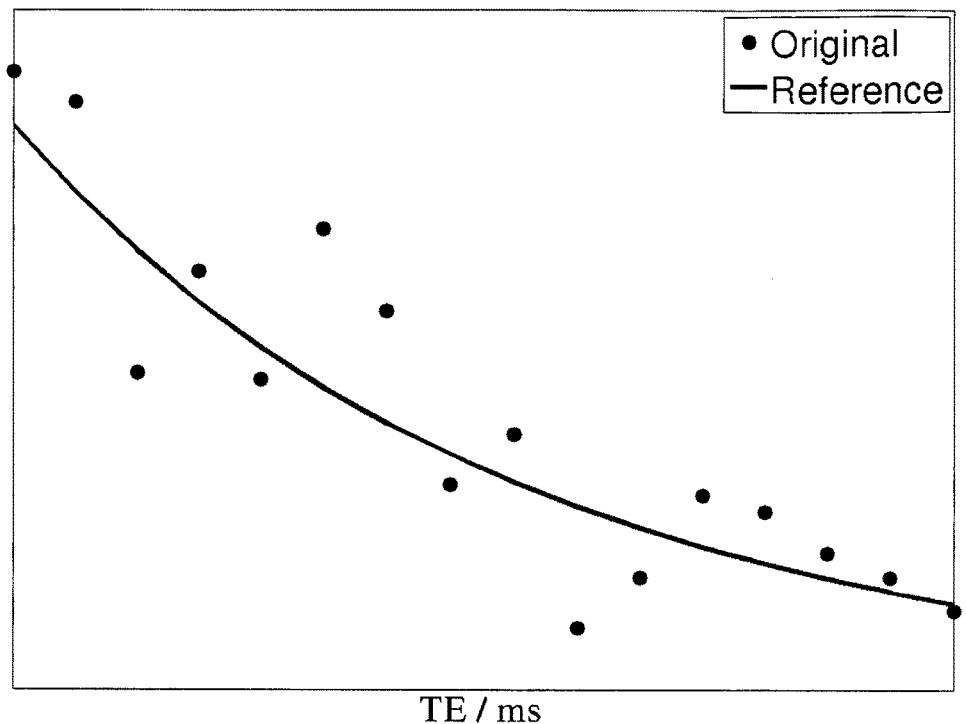
Figure 9:
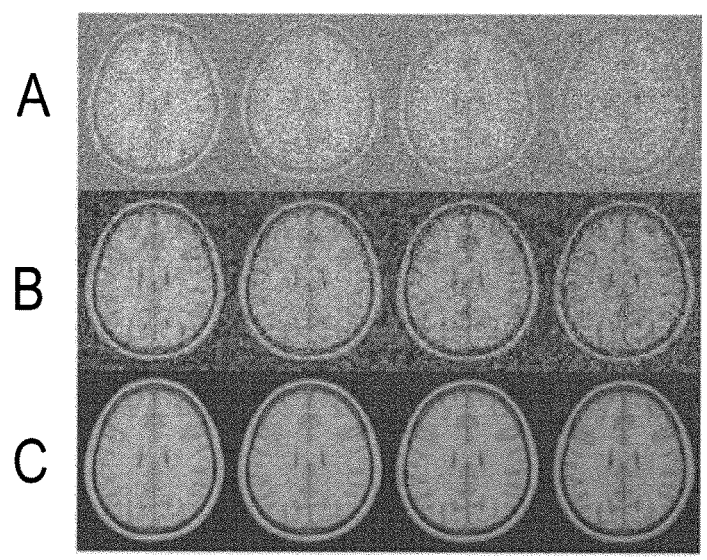
Figure 10:
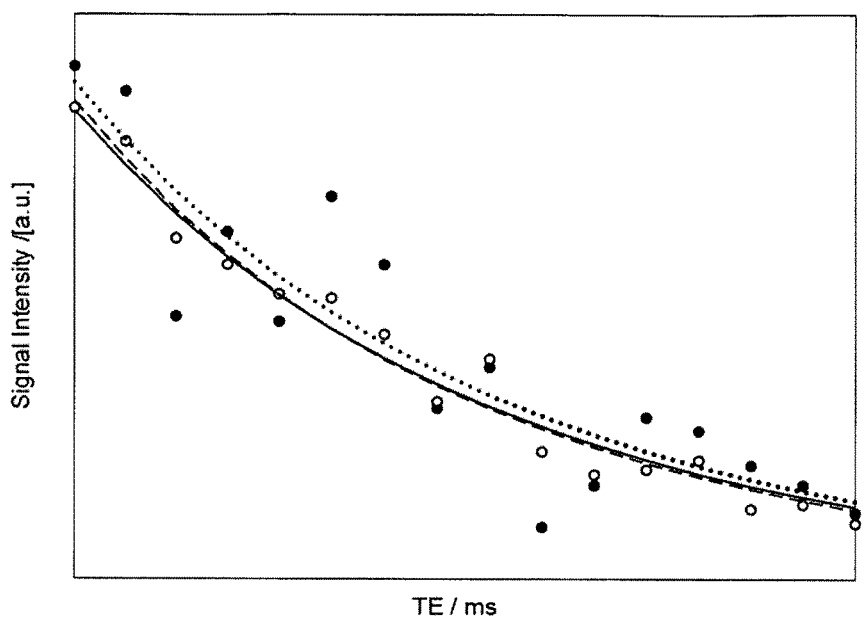

In a first example of applying the invention, the gain in SNR by application of 'standard AWESOME' to a series of 2D spin-echo MR images is demonstrated. In particular, the images of the series are assumed to be recorded as a function of the echo time (TE), whereby TE increases progressively over the image series in order to quantitatively map the transverse relaxation time, $T_2$, after a voxel-by-voxel fit if the image intensity to an exponential, $S(TE)=S(0) \exp(-TE/T_2)$. To assess the performance of the method of the invention in a a situation, where the underlying ground truth is known, the noisy images were simulated from a standard brain image by adding Gaussian complex noise to the real-valued data. For simplicity, a single exponential decay was assumed for each pixel. A total of 16 echo times (M=16) were used. The resulting images, which are used as input data to the method of the invention are shown in FIG. 7, which shows a series of simulated 2D spin-echo MR images demonstrating the effect of increasing the echo time (from left to right) in an experiment to measure the transverse relaxation time, $T_2$. FIGS. 7A and 7B show the same image series with additional random noise and without noise (reference data), resp. For the sake of clarity, only results for every other TE are displayed. It is noted that a very low SNR results at the longest TE, where the signal intensity is reduced to approx. 10% of the initial intensity at TE=0. As this example relies on simulated data, the ideal case of noiseless images is also available, and can be used as a reference. FIG. 8 demonstrates the TE dependence of the signal intensity (magnitude) in a single randomly selected pixel in the simulated 2D spin-echo MR images shown in FIG. 7 as a function of the echo time (TE). Both data with additional random noise (filled circles) and the noise-less reference (solid line) are shown for comparison. The SNR improvement obtained after application of 'standard AWESOME' is demonstrated in FIG. 9 showing simulated 2D spin-echo MR images with variation of TE (take from the same simulated data as shown in FIG. 7) comparing (9A) noisy input data, (9B) denoised data by application of 'standard AWESOME' and (9C) noiseless reference data. The SNR improvement is most pronounced in images with long TE and, hence, lower intrinsic signal. For simplicity, only images simulated for the four longest echo times are shown in the Figure. Furthermore, the quantitative information contained in the signal intensity of the images is not altered by application of 'standard AWESOME', whereas the unwanted contamination of the data by random noise is substantially reduced. This is demonstrated in FIG. 10 by plotting the intensity of a randomly selected single voxel from simulated 2D spin-echo MR images versus TE. The data from original noisy images (filled circles) and from images denoised by application of 'standard AWESOME' (open circles) are shown in comparison with ideal reference data without noise (solid line). Synthetic time course computed by parameter fitting of the data before (dotted line) and after denoising (broken line) to a $T_2$ decay are also overlaid. Application of a fitting procedure to estimate the underlying system parameters—for the current image series the transverse relaxation time of the tissue assuming a mono-exponential decay as a function of TE—yielded an improved accuracy in the fitted parameter ($T_2$) after application of 'standard AWESOME'. In particular, a systematic offset in the fitted $T_2$ decay due to the presence of noise in the input data is almost entirely removed after application of 'standard AWESOME' and the fitted curve is almost indistinguishable from the reference data. It is noted that more advanced signal processing procedures, such as the inverse Laplace transformation, which are known to be particularly susceptible to the presence of noise, would even more benefit from the improved SNR.

A second example of applying the invention demonstrates an application to qMTI. Briefly, qMTI investigates the exchange of magnetization between semisolid macromolecules or membranes in a biological tissue (e.g., brain tissue) and tissue water molecules, which is mediated by cross-relaxation and/or chemical exchange. Here, a biophysical model, such as the binary spin-bath (BSB) model, is fitted to the image data to extract a set of model parameters (i.e., pool sizes, relaxation rates, and exchange rates) that quantitatively characterize the interacting spin pools. To demonstrate the application of the method of the invention, M=38 image volumes (200 μm nominal isotropic resolution) were recorded at 3 T form a post-mortem marmoset brain with a 3D fast low-angle shot (FLASH) imaging pulse sequence and pulsed off-resonance saturation with a range of different frequency offsets and RF pulse amplitudes. For routine offline (complex-valued) signal averaging, experiments were repeated 6 to 16 times (depending on the expected signal intensity), and each repetition was individually stored. As a pre-processing step, all complex-valued images were linearly registered to the first image, and the entire image series was phase-corrected (step S3 in the detailed description). The first repetition from each combination of acquisition parameters (FIG. 12a) was used as low-SNR data set to evaluate the performance of the method of the invention whereas another set of averaged image volumes was used as high-SNR reference data set. Following the procedures outlined above, the complex-valued 3D image volumes were wavelet transformed with 'symlet8' and five frequency bands (step S7 in the detailed description). Each frequency band was subdivided into seven sub-bands yielding a total of 35 sub-bands per image volume (step S12 in the detailed description).

In this example, three types of image processing were compared: (i) low-SNR non-averaged image data with no further processing, (ii) image data obtained from this low-SNR data after application of 'standard AWESOME', and (iii) image data obtained from the same low-SNR data after application of 'refined AWESOME' that additionally integrates prior knowledge. For a quantitative assessment of the individual results, the sum squared difference, $$SSD = \sum_{m=1}^{M} (I_m^\alpha - I_m^{ref})^2, \qquad (13)$$

and Spearman's rank correlation coefficient, ρ, were computed, where $I_m^\alpha$ is the average signal intensity in the preselected mask (step S12 in the detailed description) of image volume m obtained with processing procedure α (i.e., i, ii, or iii), and $I_m^{ref}$ is the corresponding average signal intensity (mask region) in the high-SNR reference. Finally, BSB model fits were performed as described in Ref. [12], and the norm of the residuals was computed assuming that fitting the high-SNR reference data yield the 'true' model parameters. For easier comparison, the SSD and the residual norm were normalized with respect to the low-SNR non-averaged result. All results are summarized in Table 1. Compared to the results obtained without denoising (α=i), application of 'standard AWESOME' (α=ii) yielded a reduction of the average SSD by approx. 35% and an improved correlation when comparing the images series with the high-resolution reference data. Similarly, the residual norms after BSB parameter fitting improved by approximately 23% and 35% in arbitrarily selected single voxels in cortical gray matter (GM) and white matter (WM), respectively.

Figure 11:
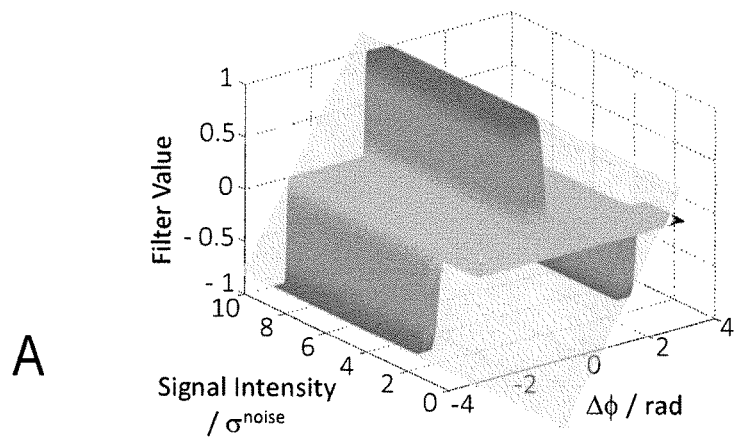
Figure 11:
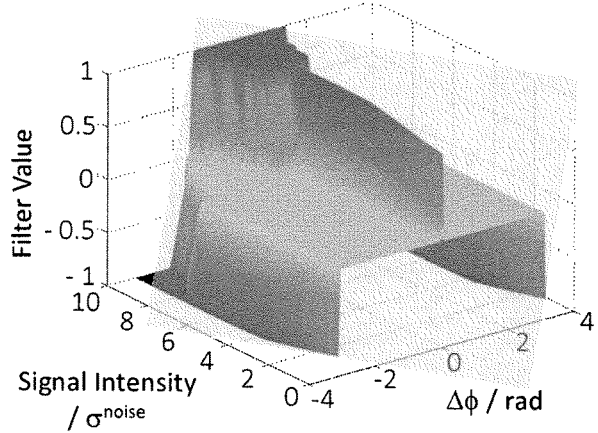

A further analysis of the experimental data revealed the presence of an additional contribution of spurious signal to the image background (probably due to weak residual spurious echoes that were not completely suppressed by gradient and RF spoiling) besides purely random noise. This ghosting artefact is characterized by a partially coherent phase component over the series ('coherent noise' contribution), which is not sufficiently suppressed upon averaging. Hence, 'refined AWESOME' (α=iii), was additionally applied to evaluate its potential of better suppression of such spurious contributions. For a better appreciation of modifications between 'standard' and 'refined AWESOME' as applied in this particular embodiment, FIG. 11 shows the corresponding transfer functions for both image-processing procedures, calculated as phase and intensity filters according to step using sigmoid curves as defined in steps S8 to S10. FIG. 11A shows the transfer function for 'standard AWESOME' based on the assumption of uniformly distributed random noise and $\sigma_\varphi$ according to step S6 in the preselected mask of the top 10% of the voxels with highest mean signal intensity obtained with step S5, and FIG. 11B shows a modified transfer function for 'refined AWESOME' to account for correlating noise. The adaptions 'refined AWESOME' were performed employing prior knowledge available from the high-SNR reference data set by a minimization procedure on the mean squared difference between the reference data and denoised data ('interior-point' algorithm). As a result, the passband of the transfer function is clearly increased for larger coefficients to reduce the risk of false classifications as 'noise' due to artificially increased phase differences whereas it is substantially decreased for smaller coefficients to improve background removal in the presence of correlated noise. To achieve a sufficiently fast optimization, the number of parameters ξ shaping the transfer function was limited to 10. The resulting slightly "choppy shape" with discontinuous changes of the transfer function (FIG. 11B) did, however, not markedly degrade its performance.

Figure 12:
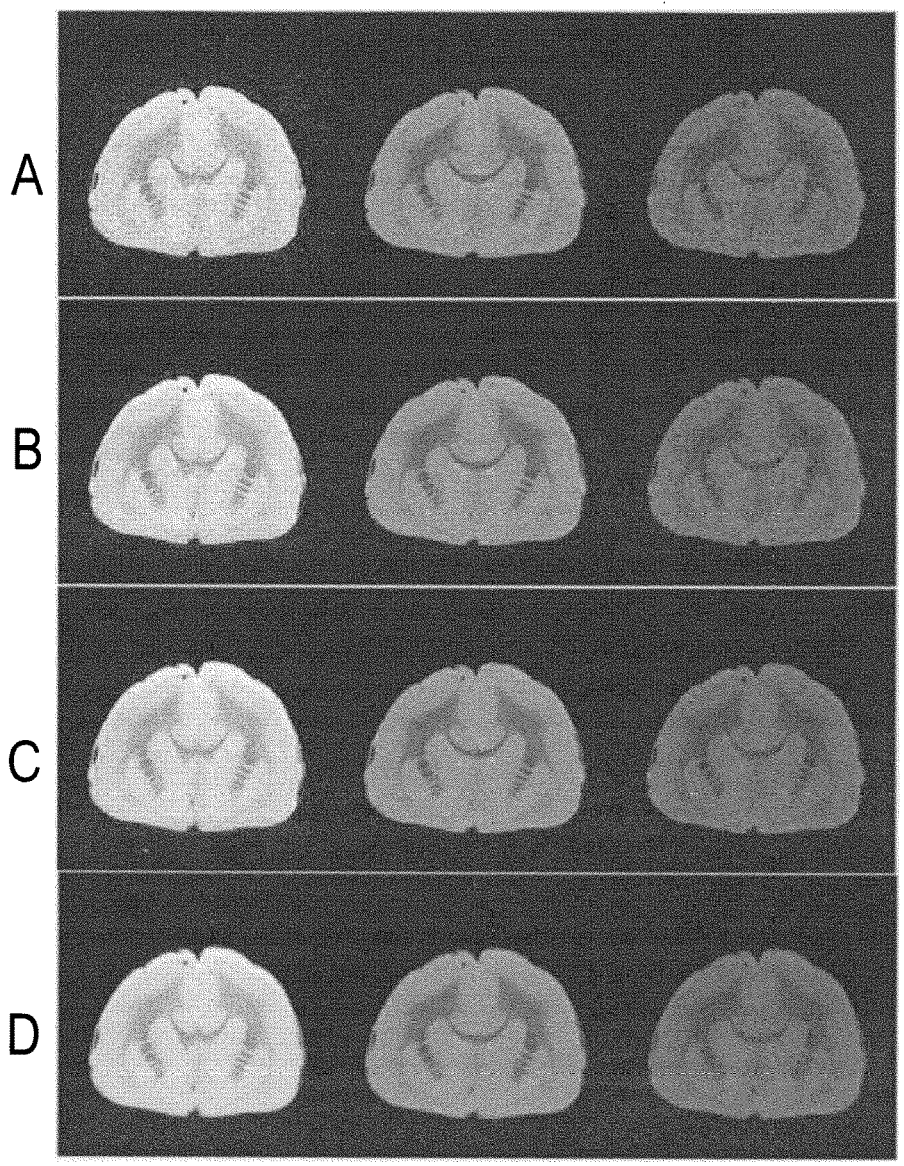
Figure 13:
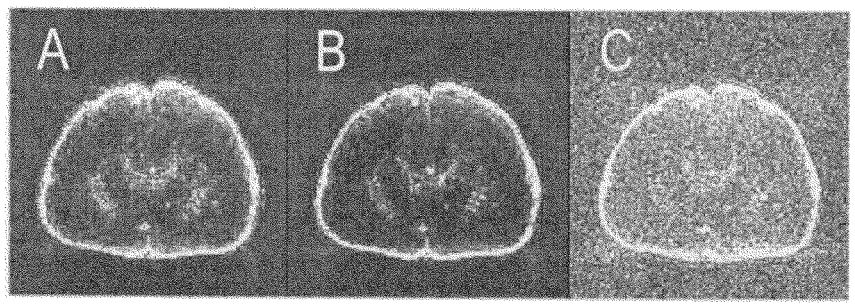

Table 1 demonstrates that the modifications used with 'refined AWESOME' did lead to improved performance as indicated by further reductions of the average SSD and residual norms after BSB parameter fitting as well as a subtle improvement of the correlation with the reference data. These improvements also become evident at visual image inspection (FIG. 12) demonstrating excellent suppression of noise and improved visibility of fine details. FIG. 12 shows axial slices from 3D qMTI volumes recorded with different saturation pulse offsets (left to right: 30.0, 6.1, and 1.2 kHz) with low-SNR input data without averaging and denoising (FIG. 12A), the result after application of 'standard AWE-SOME' (FIG. 12B), the result after application of 'refined AWESOME' (FIG. 12C), and high-SNR reference data (left to right: 6, 6, and 9 averages) (FIG. 12D). Finally, SSD maps (FIG. 13) demonstrate the presence of correlated noise in the low-SNR input data that is more efficiently removed by application of 'refined AWESOME' in comparison to 'standard AWESOME'. Maps of the sum squared difference obtained are shown after application of 'standard AWE-SOME' (FIG. 13A), and after application of 'refined AWE-SOME' in comparison (FIG. 13B) to the SSD map obtained with the low-SNR data without averaging and denoising (FIG. 13C).

TABLE 1

Indicators of the performance of the method of the invention applied to qMTI data.

| | Average SSD* | Spearman's ρ | Norm of the residuals* Gray matter | Norm of the residuals* White matter |
|---|---|---|---|---|
| High-SNR reference | — | — | 0.778 | 0.453 |
| Low-SNR data | 1 | 0.985 | 1 | 1 |
| 'Standard AWESOME' | 0.651 | 0.991 | 0.773 | 0.651 |
| 'Refined AWESOME' | 0.477 | 0.994 | 0.773 | 0.474 |

*Values normalized to the result from the low-SNR data without averaging and denoising.

A third example of a beneficial application of the invention is related to the field of fMRI. In typical functional experiments, imaging of the brain is repetitively performed, that is, mapping of an extended brain region or the entire brain is performed with a temporal resolution of 1-3 s and serial acquisition of several hundred image volumes while the subject is exposed to, e.g., audio-visual or tactile stimuli or has to perform a carefully devised task based on cognitive concepts to activate particular areas in the brain or networks of brain regions. These regions or networks are subsequently isolated from the dynamic image data employing statistical methods. Similarly, repetitive acquisitions may be performed in the absence of a task (so-called 'resting-state' fMRI) to study functional connectivity within brain networks. Typical signal changes related to a stimulus are of the order of 0.5 to 5% or even less and are, hence, often buried under nuisance contributions from thermal and/or physiological noise. These specific experimental conditions of generating long time series of data (M>100) leads to particularly favorable conditions for applying either 'standard AWESOME' or 'refined AWESOME' with an expected substantial improvement of the time-series SNR through adaptive averaging. Similar applications might also include related experimental conditions, in which image data are repetitively recorded as a function of time, e.g., in perfusion imaging with ASL or DSC techniques, blood volume mapping by VASO, or cardiac imaging and other so-called CINE-MR techniques.

Yet another example of applying the invention is related to the field of dMRI. In these experiments, the (hindered) Brownian motion or water (also referred to as self-diffusion) is measured in a tissue by applying so-called diffusion-encoding (or diffusion-weighting) gradients, for example, by variation of the strength of the diffusion-encoding gradient in serial acquisitions. If the tissue under investigation is characterized by anisotropy, the measurements are furthermore repeated with variation of the gradient direction, which leads to a characteristic variation of signal intensity reflecting the underlying structural anisotropy. Typically, a relatively large number of gradient directions is studied to extract sufficient information for reconstructing the anisotropic tissue properties (e.g., the orientation of nerve fiber bundles or the arrangement of fibers in skeletal or cardiac muscle). Realistic numbers of gradient orientations may be of the order of M=6-60 but can even exceed 200 in specific applications. In such experiments, either 'standard AWESOME' or 'refined AWESOME' may be applied (eventually, after initial applications of phase correction and/or distortion-correction procedures to remove shot-to-shot phase inconsistencies and gradient-related image distortion, resp.), to substantially improve the overall SNR of the data by adaptive averaging of data acquired from the same slice or 3D volume but with different strengths and/or orientations of the diffusion-encoding gradients.

Embodiment of MRI Device

Figure 14:
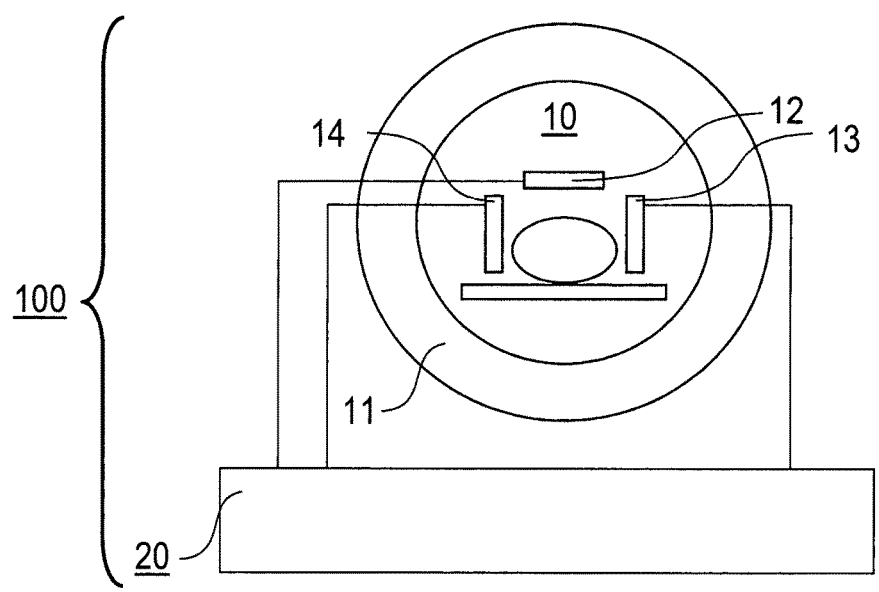
FIG. 14: schematic illustration of an MRI device according to an embodiment of the invention.

FIG. 14 schematically shows an MRI device 100 with an MRI scanner 10 including a main magnetic field device 11, at least one radiofrequency excitation coil 12, at least two magnetic field gradient coils 13 and radiofrequency receiver coils 14. Furthermore, the MRI device 100 includes a control device 20, like a computer circuit, being adapted for controlling the MRI scanner 10 for collecting the series of sets of image raw data and denoising the image data with the method according to the invention.

The features of the invention disclosed in the above description, the drawing and the claims can be of significance both individually as well as in combination or subcombination for the realisation of the invention in its various embodiments.

The invention claimed is:

1. A method of image processing of magnetic resonance (MR) images for creating de-noised MR images, comprising the steps of
    providing image data sets including multiple complex MR images,
    subjecting the multiple complex MR images to a wavelet decomposition for creating coefficient data sets of wavelet coefficients ($S_{n,m}$) representing the multiple complex MR images in a wavelet frequency domain,
    calculating normalized coefficient data sets of wavelet coefficients ($S_{n,m}^{norm}$), wherein the coefficient data sets are normalized with a quantitative amount ($\sigma_m^{noise}$) of variation of noise contributions included in the coefficient data sets ($S_{n,m}$),
    averaging the wavelet coefficients of each coefficient data set for providing averaged wavelet coefficients ($\overline{S_n}$) of the coefficient data sets,
    calculating phase difference maps ($\Delta\phi_{n,m}$) for all coefficient data sets, wherein the phase difference maps provide phase differences between a phase of each wavelet coefficient and a phase of the averaged wavelet coefficients ($\overline{S_n}$),
    calculating scaled averaged coefficient data sets of wavelet coefficients by scaling the averaged wavelet coefficients ($\overline{S_n}$) with scaling factors ($C_{n,m}$), which are obtained by comparing parts of the normalized wavelet coefficients of the normalized coefficient data sets ($S_{n,m}^{norm}$) that are in phase with the averaged wavelet coefficients ($\overline{S_n}$),
    calculating rescaled coefficient data sets of wavelet coefficients ($S_{n,m}^{new}$) by applying a transfer function ($T(|S_{n,m}^{norm}|, \Delta\phi_{n,m})$) on the coefficient data sets ($S_{n,m}$) and on the scaled averaged coefficient data sets, wherein the transfer function includes combined amplitude and phase filters, each depending on the normalized coefficient data sets ($S_{n,m}^{norm}$) and the phase difference maps ($\Delta\phi_{n,m}$), respectively, and
    subjecting the rescaled coefficient data sets to a wavelet reconstruction ($S_{n,m}^{new}$) for providing the denoised MR images.

2. The method according to claim 1, wherein the step of providing the image data sets of multiple complex MR images includes:
    providing a series of MR image raw data, and
    calculating a quantitative amount ($\sigma_\phi$) of variation of a phase of signal contributions in the MR image raw data.

3. The method according to claim 2, wherein the step of providing the image data sets of multiple complex MR images further includes at least one of:
    spatial registration of the MR image raw data, and
    phase correction of the MR image raw data for compensating a consistent time evolution over the series of MR image raw data related to a collection of the MR image raw data.

4. The method according to claim 2, wherein
    the amplitude and phase filters included in the transfer function ($T(|S_{n,m}^{norm}|, \Delta\phi_{n,m})$) are constructed on the basis of sigmoid functions and the quantitative amount ($\sigma_\phi$) of variation of the phase of signal contributions in the MR image raw data.

5. The method according to claim 1, wherein
    the phase filter included in the transfer function ($T(|S_{n,m}^{norm}|, \Delta\phi_{n,m})$) comprises mirrored phase dependent portions.

6. The method according to claim 1, wherein the quantitative amount of variation of noise contributions is a standard deviation ($\sigma_m^{noise}$) of noise contributions included in the coefficient data sets ($S_{n,m}$).

7. The method according to claim 1, wherein a standard deviation ($\sigma_m^{noise}$) of noise contributions included in the coefficient data sets ($S_{n,m}$) is calculated by the steps of
    calculating a standard deviation ($\sigma_m$) of absolute wavelet coefficients ($S_{n,m}$),
    separating of noise-containing and information-containing coefficients by applying a mask depending on the standard deviation ($\sigma_m$), and
    calculating the standard deviation ($\sigma_m^{noise}$) of the noise-containing coefficients.

8. The method according to claim 7, wherein
    the noise-containing coefficients are subjected to a statistical analysis for obtaining a distribution of intensity and phase of the noise-containing coefficients and a potential correlation of the noise over an image series.

9. The method according to claim 8, wherein
    the transfer function ($T(|S_{n,m}^{norm}|\Delta\phi_{n,m})$) is constructed in dependency on the distribution of intensity and phase of the noise-containing coefficients.

10. The method according to claim 1, wherein
    the wavelet decomposition is calculated with at least three frequency bands each including one sub-band for 1D image data, three sub-bands for 2D image data or seven sub-bands for 3D image data.

11. The method according to claim 10, wherein
    the step of calculating the normalized coefficient data sets of wavelet coefficients ($S_{n,m}$) is modified such that the coefficient data sets are normalized with a sub-band specific standard deviation ($\sigma_{n,m}^{noise}$) of noise contributions of the coefficient data sets ($S_{n,m}$) included in the sub-bands of the wavelet decomposition, and the phase difference maps, the scaling factors and the transfer function are calculated on the basis of a sub-band specific standard deviation ($\sigma_{n,m}^{noise}$).

12. A method of magnetic resonance imaging of an object, comprising the steps of collecting a series of MR image raw data for obtaining multiple complex MR images, and subjecting the MR images to an image processing method according to claim 1.

13. An MRI device configured for creating a sequence of MR images of an object under investigation, comprising an MRI scanner including a main magnetic field device, at least one radiofrequency excitation coil, magnetic field gradient coils and at least one radiofrequency receiver coil, and a control device configured for controlling the MRI scanner for collecting a series of sets of image data and denoising the sequence of MR images with the method according to claim 1.

14. A computer program residing on a computer-readable medium, with a program code which, when executed on a computer, carries out the method according to claim 1.

15. An apparatus comprising a computer-readable storage medium containing program instructions which, when executed on a computer, carry out the method according to claim 1.

* * * * *